United States Patent
Pasricha et al.

(10) Patent No.: US 12,226,433 B2
(45) Date of Patent: Feb. 18, 2025

(54) TREATMENT OF IRRITABLE BOWEL SYNDROME WITH MOLYBDENUM

(71) Applicant: The Johns Hopkins University, Baltimore, MD (US)

(72) Inventors: Pankaj J. Pasricha, Ellicott City, MD (US); Lian Sheng Liu, Ellicott City, MD (US); Qian Li, Ellicott City, MD (US); Alfred Spormann, Stanford, CA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/266,551

(22) PCT Filed: Jul. 22, 2019

(86) PCT No.: PCT/US2019/042743
§ 371 (c)(1),
(2) Date: Feb. 5, 2021

(87) PCT Pub. No.: WO2020/033130
PCT Pub. Date: Feb. 13, 2020

(65) Prior Publication Data
US 2021/0308174 A1 Oct. 7, 2021

Related U.S. Application Data

(60) Provisional application No. 62/714,807, filed on Aug. 6, 2018.

(51) Int. Cl.
| | | |
|---|---|---|
| *A61K 33/00* | (2006.01) | |
| *A61K 9/00* | (2006.01) | |
| *A61K 33/24* | (2019.01) | |
| *A61P 1/00* | (2006.01) | |
| *A61P 1/04* | (2006.01) | |
| *A61P 1/06* | (2006.01) | |
| *A61P 3/02* | (2006.01) | |
| *A61P 29/00* | (2006.01) | |

(52) U.S. Cl.
CPC ............ *A61K 33/00* (2013.01); *A61K 9/0053* (2013.01); *A61K 33/24* (2013.01); *A61P 1/00* (2018.01); *A61P 1/04* (2018.01); *A61P 1/06* (2018.01); *A61P 29/00* (2018.01); *A61P 3/02* (2018.01)

(58) Field of Classification Search
None
See application file for complete search history.

(56) References Cited

U.S. PATENT DOCUMENTS

| | | | |
|---|---|---|---|
| 5,399,363 A | 3/1995 | Liversidge et al. | |
| 5,466,468 A | 11/1995 | Schneider et al. | |
| 5,543,158 A | 8/1996 | Gref et al. | |
| 5,580,579 A | 12/1996 | Ruddy et al. | |
| 5,629,001 A | 5/1997 | Michael et al. | |
| 5,641,515 A | 6/1997 | Ramtoolz | |
| 5,725,871 A | 3/1998 | Illum | |
| 5,756,353 A | 5/1998 | Debs | |
| 5,780,045 A | 7/1998 | McQuinn et al. | |
| 5,792,451 A | 8/1998 | Sarubbi et al. | |
| 5,804,212 A | 9/1998 | Illum | |
| 6,613,308 B2 | 9/2003 | Bartus et al. | |
| 6,737,514 B1 | 5/2004 | Wang et al. | |
| 9,561,194 B2 | 2/2017 | Schiffrin et al. | |
| 2003/0130217 A1 | 7/2003 | Raz et al. | |
| 2010/0024748 A1 | 2/2010 | Chae et al. | |
| 2010/0247489 A1* | 9/2010 | Saur-Brosch | A61K 31/122 424/617 |
| 2014/0037603 A1 | 2/2014 | Bolster | |
| 2016/0243172 A1 | 8/2016 | Cook et al. | |
| 2017/0209509 A1* | 7/2017 | Oda | A61P 1/14 |

FOREIGN PATENT DOCUMENTS

| | | | |
|---|---|---|---|
| AU | 2017101183 A4 | 10/2017 | |
| CA | 2444548 C * | 6/2016 | ............ A23L 33/40 |
| WO | WO-9956553 A1 * | 11/1999 | ............ A01N 63/00 |
| WO | 20100114864 A1 | 10/2010 | |

OTHER PUBLICATIONS

Newport et al.("The mechanisms of inhibition of Desulfovibrio and Desulfotomaculum species by selenite and molybdate", Journal of Applied Bacteriology, 1988, vol. 65, p. 419-423) (Year: 1988).*
Takenaga et al., 1998 Microparticle resins as a potential nasal drug delivery system for insulin., J Control Release 52:81-7.
Mathiowitz et al., 1997 Biologically erodable microspheres as potential oral drug delivery systems., Nature 386 (6623):410-4.

* cited by examiner

*Primary Examiner* — Sin J Lee
(74) *Attorney, Agent, or Firm* — Fox Rothschild LLP

(57) ABSTRACT

Described are methods for treating or preventing IBS in subjects by administering molybdenum or a salt thereof to subjects having or prone of getting IBS. The molybdenum has been shown to treat or prevent IBS in subjects administered this agent when compared to reference subjects not administered molybdenum.

16 Claims, 1 Drawing Sheet

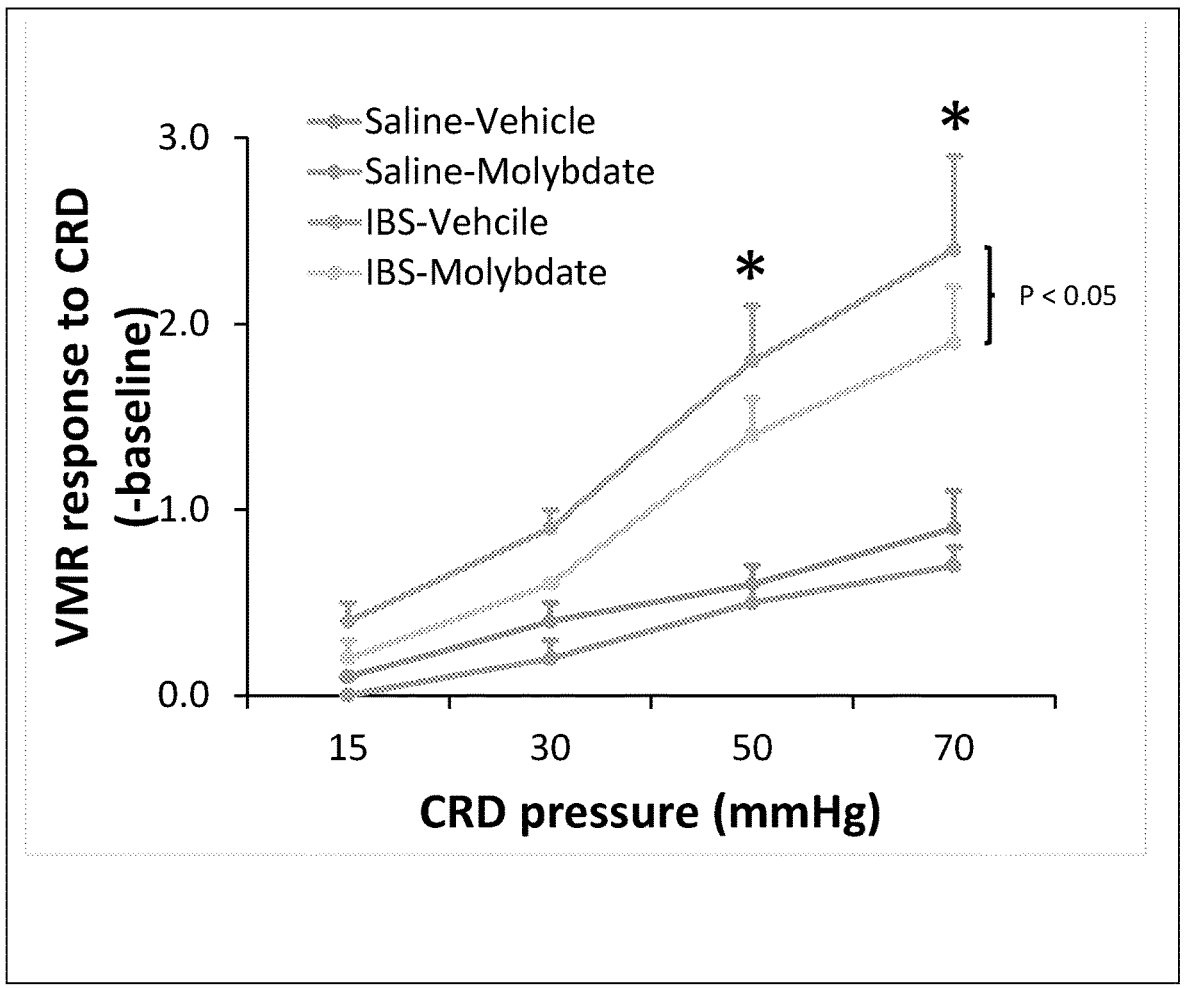

TREATMENT OF IRRITABLE BOWEL SYNDROME WITH MOLYBDENUM

CROSS-REFERENCE TO RELATED APPLICATION

This application is a National Stage Application filed under 35 U.S.C. § 371, of International Application No. PCT/US2019/042743, filed Jul. 22, 2019, which claims the benefit of and priority to U.S. Provisional Application No. 62/714,807, filed Aug. 6, 2018. The entire contents of which applications are incorporated herein by reference in their entirety.

BACKGROUND OF THE INVENTION

The pathogenesis of irritable bowel syndrome is not fully understood and consequently finding the right therapeutic targets for drug development has been difficult. In recent years, there is growing evidence that altered microbiota may play a role in the development of this syndrome which has led to great interest in microbiota-modifying approaches. These include probiotics, diets and the FDA-approved luminal antibiotic, rifaximin, for this purpose. However, these are not completely satisfactory, either because of lack of efficacy (probiotics), sustainability (diet) or frequent relapses (rifaximin). There is therefore a need for a safe and effective agent that specifically modulates microbiota in a manner that is effective for relieving symptoms of irritable bowel syndrome (IBS).

SUMMARY OF THE INVENTION

One embodiment of the present invention are methods for treating or preventing irritable bowel syndrome (IBS) in a subject. These methods comprise the steps of administering molybdenum, a salt, a solvate, a stereoisomer, or oxidative state thereof, to a subject having or prone of getting IBS and treating or preventing the IBS of the subject when compared to a reference subject not administered the molybdenum. Any suitable molybdenum including a pharmaceutical composition thereof may be used in the methods of the present invention. Any suitable form of administration may be used such as oral administration. The method of the present invention may further comprise the step of inhibiting the growth of bacteria in the gut of the subject assisting in the treating and preventing IBS in a subject. *Desulfovibrio* is an example of a sulfate reducing bacteria located in the gut of a subject that was determined to be inhibited by molybdenum. The methods of the present invention treat or prevent IBS of the subject by reducing a hyperalgesia in the subject, as an example.

Another embodiment of the present invention are methods for treating the pain of IBS in a subject. The methods comprise the steps of administering molybdenum or salt thereof to a subject having or prone of getting IBS and treating the pain of IBS of the subject when compared to a reference subject not administered the molybdenum.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease, such as irritable bowel syndrome.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features.

By "disease" is meant any condition or disorder that damages or interferes with the normal function of a cell, tissue, or organ.

By "effective amount" is meant the amount of a required agent (or active compound) to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "molybdenum" is meant a chemical element with the symbol Mo and atomic number 42 and having different oxidation states. For example, molybdate is a compound containing an oxoanion with molybdenum in its highest oxidation state of 6.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Such treatment will be suitably administered to subjects, particularly humans, suffering from, having, susceptible to, or at risk for irritable bowel syndrome or disease, disorder, or symptom thereof. Determination of those subjects "at risk" can be made by any objective or subjective determination by a diagnostic test or opinion of a subject or health care provider (e.g., genetic test, enzyme or protein marker, a marker, family history, and the like).

BRIEF DESCRIPTION OF THE DRAWINGS

FIG. 1 Colonic treatment of sodium molybdate reduced hyperalgesia in mouse model of IBS. Molybdate was infused into cecum for 7 days. The pain sensitivity was assessed by VMR response to CRD. Data were presented as mean f SEM (n=5-6). Three-WAY ANOVA reveal main effect of model: P<0.001, main effect of treatment P<0.05 and main effect of pressure P<0.001. Post hoc test showed significant difference between IBS-vehicle and IBS-molybdate (P<0.05). *: significantly different from Saline-Vehicle at same pressure determined by Student-Newman-keuls post hoc test.

DETAILED DESCRIPTION OF THE INVENTION

Molybdate functions as a cofactor for formate dehydrogenase in several microbiota species, such as sulfate-reducing bacteria species. Excess of molybdate inhibits the sulfate-reducing bacteria. Studies have showed an increase of the sulfate-reducing bacteria in the stool of irritable bowel syndrome (IBS) patients, which may be related to the hyperalgesia in these patients. Thus, the inventors hypothesize that treatment with molybdate will reduce sulfate-reducing bacteria (SRB), resulting in attenuation on pain sensitivity in IBS mouse model. To test the hypothesis, the inventors conducted a study to determine the effect of colonic infusion of molybdate on the pain sensitivity in IBS mouse model.

IBS mice were generated by colorectal infusion of 0.5% acetic acid (20 µl) at postnatal day 10. The mice were then allowed to grow up until adult. The adult IBS and control mice were undergone a surgery to insert a catheter into the cecum. The catheter made from PE10 tubing with 8 cm long. It was insert into cecum about 0.5 cm and then tunneled to the back of the mouse after sutured on the cecum wall ensuring no cecum content leaking. Then, a pair of electrodes were inserted into the external oblique (abdominal) muscle for pain sensitivity test. The mice received 0.2 ml sodium molybdate (10 mg/ml) through cecal infusion starting on the day after surgery for 7 days. One day after the last infusion, a visceral motor reflex (VMR) response to colorectal distention (CRD) was conducted to assess the pain sensitivity. A balloon was inserted into colorectum through the anus for CRD. The VMR is measured using an electromyographic (EMG) recording that response to CRD with 15, 30, 50 and 70 mmHg. To assess the microbiota, stool were collected before and after the molybdate treatment. Microbiome were examined by 16S rRNA sequencing.

The results of the 16S rRNA sequencing revealed that at least one of sulfate-reducing bacteria, *Desulfovibrio*, was reduced in both molybdate treated control and IBS group, but not saline treated groups. These data suggested that treatment with molybdate reduced SRBs. Furthermore, treatment with molybdate significantly attenuated pain sensitivity as measured with VMR response to CRD. As shown in FIG. 1, IBS mice have significantly higher VMR response, which was significantly reduced by treatment with molybdate. On the other hand, although a slightly lower response was observed in molybdate treated control mice, there were no significant different between saline and molybdate treated mice in pain sensitivity. Together, the present results demonstrate that colonic treatment with molybdate reduces hyperalgesia in the IBS mouse model, which could be mediated by reduction of sulfate-reducing bacteria. The present study provide evidence that molybdate can be used for therapy of IBS and other chronic GI conditions.

Embodiments of the disclosure concern methods and/or compositions for treating and/or preventing or treating chronic GI conditions such as IBS in which inhibition of the growth of one or more microbiota species, such as sulfate-reducing bacteria species, is directly or indirectly related. In certain embodiments, individuals with a GI condition such as IBS is treated with an inhibitor of one or more microbiota species, such as sulfate-reducing bacteria species, and in specific embodiments an individual with a GI condition, such as IBS, is provided molybdenum, or a salt, a solvate, or a stereoisomer (i.e., an inhibitor of the growth of one or more microbiota species, such as sulfate-reducing bacteria species).

In certain embodiments, the level to which an agent such as molybdenum or a salt thereof may be any level so long as it provides amelioration of at least one symptom of a GI condition, including IBS. An individual known to have IBS, suspected of having IBS, or at risk for having IBS may be provided an agent such as molybdenum or a salt thereof. Those at risk for IBS may be those individuals having one or more genetic factors, may be of advancing age, and/or may have a family history, for example.

In particular embodiments of the disclosure, an individual may be given a second agent for IBS therapy in addition to an agent such as molybdenum or a salt thereof. When combination therapy is employed with an agent that inhibits the growth of one or more microbiota species, such as sulfate-reducing bacteria species, the additional therapy may be given prior to, at the same time as, and/or subsequent to that agent.

Pharmaceutical Preparations

Pharmaceutical compositions of the present invention comprise an effective amount of one or more an agent that inhibits the growth of one or more microbiota species, such as sulfate-reducing bacteria species such as molybdenum or a salt thereof including molybdate, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one an agent (including molybdenum or a salt thereof) that inhibits the growth of one or more microbiota species, such as sulfate-reducing bacteria species or an additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

An agent (such as molybdenum, or a salt, a solvate, or a stereoisomer that inhibits the growth of one or more microbiota species, such as sulfate-reducing bacteria species may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The molybdenum or a salt thereof may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art. In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include molybdenum or a salt thereof one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the molybdenum or a salt thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In one embodiment of the present disclosure, the molybdenum or a salt thereof are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, molybdenum or a salt thereof may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543, 158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound molybdenum or a salt thereof may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating irritable bowel syndrome (IBS) in a subject having IBS comprising the steps of:
    inhibiting growth of bacteria in a gut of the subject, wherein the bacteria are sulfate-reducing bacteria by administering for colonic treatment molybdenum, or a salt, a solvate, or a stereoisomer thereof in a dose amount of at least 100 microgram/kg of body weight to the subject; thereby, treating the IBS of the subject.

2. The method of claim 1, wherein the molybdenum or the salt, the solvate, or the stereoisomer thereof is formulated into a pharmaceutical composition.

3. The method of claim 1, wherein the molybdenum salt is molybdate.

4. The method of claim 1 wherein the molybdenum or the salt, the solvate, or the stereoisomer thereof is administered orally.

5. The method of claim 1, wherein the sulfate-reducing bacteria are *Desulfovibrio*.

6. The method of claim 1 wherein treating the IBS of the subject comprises reducing a hyperalgesia in the subject.

7. The method of claim 1, wherein the subject is identified as having the irritable bowel syndrome and the identified subject is selected for administering the molybdenum, or the salt, the solvate, or the stereoisomer thereof.

8. The method of claim 1 wherein the molybdenum, or the salt, the solvate, or the stereoisomer thereof is administered in a dose amount of at least 500 microgram/kg of body weight to the subject.

9. A method for treating the pain of irritable bowel syndrome (IBS) comprising the steps of:
    inhibiting growth of bacteria in a gut of a subject having IBS, wherein the bacteria are sulfate-reducing bacteria, by administering molybdenum or a salt, a solvate, or a stereoisomer thereof in a dose amount of at least 100 microgram/kg of body weight to the subject, thereby treating the pain from the IBS of the subject.

10. The method of claim 9, wherein the molybdenum or the salt, the solvate, or the stereoisomer thereof is formulated into a pharmaceutical composition.

11. The method of claim 9, wherein the molybdenum salt is molybdate.

12. The method of claim 9 wherein the molybdenum or the salt, the solvate, or the stereoisomer thereof is administered orally.

13. The method of claim 9 wherein the sulfate-reducing bacteria are *Desulfovibrio*.

14. The method of claim 9 wherein treating the pain from IBS of the subject comprises reducing a hyperalgesia in the subject.

15. A method for treating irritable bowel syndrome (IBS) in a subject having IBS, comprising:
    administering for colonic treatment molybdenum, or a salt, a solvate, or a stereoisomer thereof in a dose amount of at least 100 microgram/kg of body weight to the subject, thereby, treating or preventing the IBS of the subject.

16. The method of claim 15 wherein the molybdenum, or the salt, the solvate, or the stereoisomer thereof is administered in a dose amount of at least 500 microgram/kg of body weight.

* * * * *